(12) United States Patent
Kramer

(10) Patent No.: US 6,448,434 B1
(45) Date of Patent: Sep. 10, 2002

(54) PROCESS FOR MAKING AMMONIUM GLYPHOSATE POWDER

(75) Inventor: Richard M. Kramer, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/624,949

(22) Filed: Jul. 25, 2000

Related U.S. Application Data (60) Provisional application No. 60/146,281, filed on Jul. 29, 1999.

(51) Int. Cl.[7] .................................................. C07F 9/38
(52) U.S. Cl. .......................................... 562/17; 504/206
(58) Field of Search .............................. 562/17; 504/206

(56) References Cited

U.S. PATENT DOCUMENTS

| | | | |
|---|---|---|---|
| 5,047,079 A | 9/1991 | Djafar et al. | 71/86 |
| 5,070,197 A | 12/1991 | Chin et al. | 544/11 |
| 5,266,553 A | 11/1993 | Champion | 504/206 |
| 5,324,708 A | 6/1994 | Moreno | 504/206 |
| 5,410,075 A | 4/1995 | Moreno et al. | 562/17 |
| 5,612,285 A | 3/1997 | Arnold | 504/206 |
| 5,614,468 A | 3/1997 | Kramer et al. | 504/206 |
| 5,633,397 A | 5/1997 | Gillespie et al. | 562/17 |
| 5,656,572 A | * 8/1997 | Kuchikata et al. | 504/206 |
| 5,693,593 A | 12/1997 | Arnold | 504/206 |
| 5,716,903 A | 2/1998 | Kramer et al. | 504/206 |

FOREIGN PATENT DOCUMENTS

| | | | | |
|---|---|---|---|---|
| EP | 0 378 985 | 7/1990 | | A01N/57/20 |
| EP | 0 582 561 | 2/1994 | | A01N/57/20 |
| WO | WO87/04595 | 8/1987 | | A01N/57/20 |
| WO | WO90/07275 | 7/1990 | | A01N/57/20 |
| WO | WO92/12637 | 8/1992 | | A01N/57/20 |
| WO | WO94/10844 | 5/1994 | | A01N/57/20 |
| WO | WO96/40696 | 12/1996 | | C07F/9/38 |

OTHER PUBLICATIONS

CA:93:170277 abs of J Chem Eng Jpn by Okuda 13(3) pp 219–225 1980.*
CA:109:2308 abs of Funti to Kogyo by Takahashi 19(10) pp 35–40 1987.*

* cited by examiner

Primary Examiner—Jean F. Vollano
(74) Attorney, Agent, or Firm—Senniger, Powers, Leavitt & Roedel; Joseph A. Schaper (57) ABSTRACT

A process is provided for preparing ammonium glyphosate powder suitable for downstream processing by extrusion to make a granular formulation comprising ammonium glyphosate and surfactant. The process comprises (a) mixing (i) solid particulate glyphosate acid, (ii) water in an amount of about 0.5 to about 3 parts by weight per part by weight of glyphosate acid, and (iii) a base that supplies ammonium cations, in an amount of about 0.8 to about 1.25 mole equivalents of ammonia per mole of glyphosate acid, to form an aqueous reaction medium; (b) allowing the glyphosate acid to react with the base in the reaction medium to form a reaction product comprising a concentrated aqueous solution of ammonium glyphosate; (c) drying the reaction product, for example with a drum dryer, to recover a particulate solid; and (d) accelerating the particulate solid in a turbulent high-velocity gas stream, for example in a jet mill, to form by particle-particle attrition an ammonium glyphosate powder having a mean particle size of about 5 to about 20 μm.

34 Claims, 1 Drawing Sheet

Figure 1

PROCESS FOR MAKING AMMONIUM GLYPHOSATE POWDER

This application claims the benefit of U.S. Provisional Application No. 60/146,281 filed Jul. 29, 1999.

FIELD OF THE INVENTION

The present invention relates to preparation of a herbicidal formulation useful in agriculture and in other situations where control of weeds or other vegetation is desired. In particular, it relates to preparation of a herbicidal active ingredient, namely N-phosphonomethylglycine (glyphosate) in the form of the ammonium salt thereof, as an intermediate useful in further processing together with a surfactant to make a water-soluble or water-dispersible dry particulate herbicidal formulation.

BACKGROUND OF THE INVENTION

Glyphosate herbicides, especially herbicides comprising a water-soluble salt of glyphosate, are well known. Specifically, the monoammonium salt of glyphosate is disclosed as a useful herbicide for example in U.S. Pat. No. 4,405,531 to Franz. Unless the context demands otherwise, "ammonium glyphosate" herein refers to the monoammonium salt of glyphosate, which has the chemical formula it being understood that the mole ratio of ammonium cations to glyphosate anions in such a salt is not necessarily exactly 1. A slight molar excess of either ammonium cations or glyphosate anions, for example providing a mole ratio of about 0.8 to about 1.25, is not inconsistent with the term "ammonium glyphosate" as used herein.

Ammonium glyphosate is the primary salt of choice in the preparation of dry glyphosate herbicide formulations. A "dry" formulation herein is a composition that is solid, usually particulate, wherein particles are either aggregated as in a granular composition or non-aggregated as in a powder. The word "dry" in this context does not imply that the formulation is necessarily free of water or other liquid, only that it is dry to the touch. Dry formulations can contain up to about 5% by weight of water, but more typically the water content is less than about 1%, for example about 0.5% or lower.

Dry formulations of glyphosate herbicides, like the corresponding liquid (normally aqueous) formulations, typically contain one or more surfactants in addition to the glyphosate salt. Surfactants are important components of glyphosate formulations because, when a glyphosate formulation is diluted, dissolved or dispersed in water for application by spraying to foliage of plants, the surfactants assist in retention of droplets of the spray by the foliage, adhesion of the spray droplets to the foliar surface and penetration of the glyphosate through the hydrophobic cuticle that covers the foliar surface, by these means and possibly in other ways enhancing herbicidal effectiveness of the glyphosate spray. Specific surfactant types differ greatly in the degree to which they enhance herbicidal effectiveness of glyphosate, and it is therefore important to select a suitable surfactant or combination of surfactants, as demonstrated by Wyrill & Burnside, *Weed Science* 25, 275–287, 1977.

The optimum amount of surfactant for delivering the desired herbicidal effectiveness is typically in the range of about 0.2 to about 1 part by weight of surfactant per part by weight of glyphosate, expressed as acid equivalent (a.e.). When it is desired to formulate the glyphosate herbicide in dry form, it can be difficult to load such an amount of surfactant into the formulation without the formulation becoming sticky, having a tendency to cake or lacking good pouring or flow properties.

At least three approaches are known in the art to overcoming the problems of providing a sufficient amount of surfactant in a dry glyphosate formulation. The first and most straightforward is to add an inert particulate carrier that can absorb or adsorb the surfactant to a sufficient degree to avoid the problems mentioned above. The carrier can be insoluble but dispersible in water, as in the case for example of particulate silica, or it can be soluble in water, as in the case for example of ammonium sulfate. However, the addition of such a carrier inevitably reduces the maximum loading of glyphosate herbicide that can be accommodated in the formulation and for this reason adds substantially to the cost per unit of glyphosate a.e. of the resulting formulation. In this regard it should be recognized that the cost of processing is a significant element in the cost of a dry formulation, and the cost of processing is dictated by the volume of product produced. A product that has to be produced in high volume because its loading of active ingredient is low therefore suffers a significant penalty in cost per unit of active ingredient.

A second approach, as illustrated by U.S. Pat. No. 4,931,080 to Chan & Djafar, is to select a surfactant that is solid at ambient temperature. In this approach the surfactant is melted before mixing with particulate glyphosate herbicide and water, so that upon drying and cooling the surfactant solidifies to form a matrix surrounding the herbicide particles. There is no need for an inert carrier. Unfortunately the list of surfactants that are solid at ambient temperature excludes many surfactants that are among the most effective in potentiating glyphosate herbicidal activity.

A third approach, therefore, as illustrated by U.S. Pat. No. 5,656,572 to Kuchikata et al. (the '572 patent), is to select a surfactant that is liquid at ambient temperature and to ensure that the glyphosate herbicide particles themselves absorb or adsorb a sufficient amount of surfactant to avoid the problems of stickiness, caking and poor flowability. The '572 patent teaches that this can be achieved most readily if the surfactant selected is one that gels when added to water. However, it is also clear that the absorption and/or adsorption properties of the glyphosate herbicide particles greatly influence the amount of a liquid surfactant that can be included in a formulation.

Ammonium glyphosate is the preferred salt for use in preparing dry glyphosate formulations for a number of reasons, but perhaps mainly for the reason that ammonium glyphosate is relatively non-hygroscopic. Salts favored for preparation of aqueous formulations, such as the isopropylammonium salt or the trimethylsulfonium salt, are very difficult to dry down to a crystalline state and, once dry, have a strong tendency to reabsorb water. The sodium salt, disclosed to be useful in dry glyphosate herbicide formulations for example in International Patent Application No. WO 87/04595, is much less hygroscopic than these salts but nonetheless requires packaging with a very water-impermeable material to avoid absorption of water vapor from the atmosphere and consequent loss of free-flowing properties. U.S. Pat. No. 5,324,708 to Moreno et al. discloses a process for preparing a non-hygroscopic monoammonium glyphosate; however, dry ammonium glyphosate prepared by any known process is adequately non-hygroscopic for most practical purposes.

U.S. Pat. No. 5,266,553 to Champion & Harwell discloses a process for preparing a dry water-soluble composition comprising a salt of a herbicidal compound that includes a carboxylic acid functionality. This process comprises forming an aqueous solution or slurry of such a salt by reacting the herbicidal compound with a neutralizing base in the presence of water, and thereafter removing the water to provide the dry salt. The process is directed particularly at substituted benzoic acid herbicides and phenoxy-substituted carboxylic acid herbicides, but is said to be useful also for glyphosate. As indicated below, dry ammonium glyphosate powder prepared by a slurry reaction process has proved generally unsuitable for downstream formulation with surfactant.

Commercial herbicides in the form of dry water-soluble granules containing ammonium glyphosate together with a liquid surfactant include Roundup® Dry, Roundup® Max and Rival® herbicides, marketed by Monsanto Company in several countries.

Numerous granulation processes have been disclosed that are suitable for preparing water-soluble or water-dispersible granules of ammonium glyphosate with a liquid surfactant. One such process is pan granulation. However, a more widely used granulation process for a dry ammonium glyphosate formulation is extrusion granulation. An example of such a process is one that is broadly as described in British Patent No. 1 433 882 ("the '882 patent"), except that the primary active ingredient, namely ammonium glyphosate, is water-soluble rather than water-insoluble as in the process of the '882 patent. In this illustrative process, ammonium glyphosate is mixed with surfactant and a small amount of water to form an extrudable wet mix, which is then extruded to form strands of extrudate that break spontaneously at the point of extrusion or shortly thereafter to form short cylindrical granules, which are then dried. Drying is preferably conducted in a fluid-bed dryer. The amount of water in the wet mix is critical to the operation. If the mix is too wet, the strands of extrudate do not readily break to form discrete granules. In addition, the extrudate strands tend to stick together and/or form lumps. If the mix is too dry, the resulting granules are friable and tend to generate a significant amount of fine particulate material during drying or later, during handling of packaged granules. Optionally a rolling or tumbing step can be inserted between extruding and drying, as taught in U.S. Pat. No. 5,443,764 to Lloyd, to improve uniformity of granule size and shape.

The process by which the ammonium glyphosate, used as an intermediate in making the finished formulation, is prepared has been found to affect to a great degree the absorptive and/or adsorptive properties of particulate ammonum glyphosate with respect to a liquid surfactant. The absorbency and adsorbency properties of the ammonium glyphosate particles are especially important where, as is desirably the case, an extrusion process such as that disclosed in the above-referenced '882 patent is to be used in preparing the finished formulation.

Solid-state reaction of glyphosate acid and ammonium bicarbonate, as disclosed for example in the above-referenced '572 patent, tends to produce a particulate ammonium glyphosate having sufficient absorbency and/or adsorbency to permit satisfactory formulation with up to about 25% by weight of a liquid surfactant such as polyoxyethylene tallowamine. By contrast, reaction of an aqueous slurry of glyphosate acid with anhydrous ammonia or aqueous ammonia (ammonium hydroxide) tends to produce relatively non-absorptive or non-adsorptive ammonium glyphosate particles.

Because anhydrous and aqueous ammonia are much lower-cost sources of the ammonium cation than ammonium bicarbonate, numerous efforts have been made to develop processes wherein glyphosate acid is reacted with anhydrous or aqueous ammonia, yet wherein the resulting ammonium glyphosate is suitable for downstream formulation with surfactant, especially a liquid surfactant. To date, success has been achieved only when the reaction occurs in the presence of very small amounts of water, for example about 7 parts or less by weight of water per 100 parts by weight of dry ingredients. U.S. Pat. No. 5,614,468 to Kramer et al. discloses such a process wherein solid particulate glyphosate acid is reacted with aqueous ammonia, and U.S. Pat. No. 5,633,397 to Gillespie et al. discloses such a process wherein solid particulate glyphosate acid is reacted with anhydrous ammonia gas.

Processes wherein the acid-base reaction takes place in an aqueous medium, generating a concentrated aqueous solution of ammonium glyphosate, are easier to control than the above solid-state processes. In addition, the exothermic nature of the reaction gives rise to a need for dissipation of heat, which presents much fewer problems in an aqueous medium because of the much greater ease of ensuring adequate mixing and thereby heat exchange than is possible in a solid-state process. There is therefore a long-felt need in the art to develop an aqueous slurry process for making ammonium glyphosate wherein the ammonium glyphosate produced is suitable for downstream formulation with sufficient surfactant, in particular sufficient liquid surfactant, to provide a dry powder or granular formulation having a high degree of herbicidal effectiveness yet exhibiting good properties of storage without caking and good properties of flowability.

The present invention provides just such a process.

SUMMARY OF THE INVENTION

Figure 1:
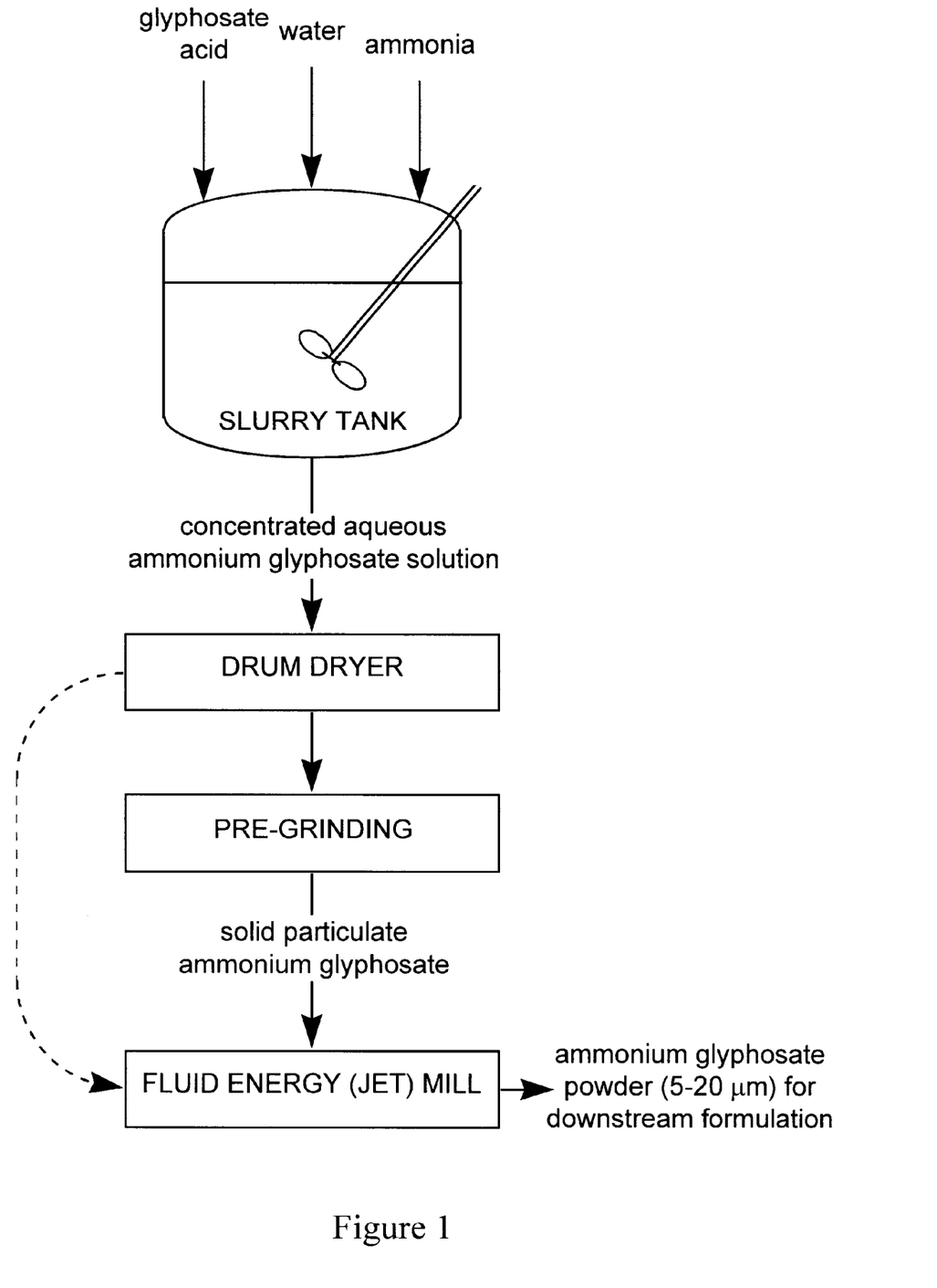
FIG. 1 shows a process flow diagram of a process of the invention.

There is now provided a process for preparing ammonium glyphosate powder comprising (a) mixing (i) solid particulate glyphosate acid, (ii) water in an amount of about 0.5 to about 3 parts by weight per part by weight of glyphosate acid, and (iii) a base that supplies ammonium cations, in an amount of about 0.8 to about 1.25 mole equivalents of ammonia per mole of glyphosate acid, to form an aqueous reaction medium; (b) allowing the glyphosate acid to react with the base in the reaction medium to form a reaction product comprising a concentrated aqueous solution of ammonium glyphosate; (c) drying the reaction product to recover a particulate solid; and (d) accelerating the particulate solid in a turbulent high-velocity gas stream, to form by particle-particle attrition an ammonium glyphosate powder having a mean particle size of about 5 to about 20 $\mu$m.

Preferably the order of mixing in step (a) is to mix solid particulate glyphosate acid and water with agitation to form a slurry, and thereafter to add to the slurry, with continued agitation, the base that supplies ammonium cations.

Preferably step (c) comprises drying the reaction product by contact thereof with a heated surface to form a solid deposit on the heated surface and thereafter recovering the solid deposit in a particulate solid form.

In a further embodiment of the invention, a process is provided for preparing a dry granular formulation comprising ammonium glyphosate and one or more surfactants, comprising steps (a) to (d) as described immediately above, followed by (e) mixing about 75 to about 90 parts by weight of the ammonium glyphosate powder with about 10 to about 25 parts by weight of one or more surfactants, and with about 3 to about 10 parts by weight of water per 100 parts by weight of ingredients other than water, to form an extrudable wet mix; (f) a granulating step that comprises extruding the wet mix to form extrudate strands that break to form moist coherent granules; and (g) drying the granules to produce the dry granular formulation. Optionally the process comprises a further step (h) of classifying the dried granules to remove or recycle granules, fragments of granules and aggregates of granules that are outside a desired size range.

Preferably the extrudable wet mix formed in step (e) is of a consistency such that the extrudate strands formed in step (f) break spontaneously upon extrusion to form the granules. However, optionally step (f) further comprises breaking or cutting the extrudate strands to form the granules. Whether or not step (f) comprises such a breaking or cutting operation, optionally step (f) comprises rolling and/or tumbling the moist granules to impart to the granules a more spherical shape and greater uniformity of size.

DETAILED DESCRIPTION OF THE INVENTION

In the first step of a preferred process of the invention, i.e., step (a) as defined above, 1 part by weight of solid particulate glyphosate acid is added to about 0.5 to about 3 parts by weight of water and sufficient agitation is applied thereto to form a slurry. The glyphosate acid is preferably evenly dispersed in the slurry, but agglomeration of glyphosate acid particles into small aggregates is generally not detrimental. The relative amounts of water and glyphosate acid used to make the slurry are not narrowly critical within the range indicated above. However, it is generally desirable to produce, in step (b) that follows, an ammonium glyphosate solution of a high concentration, for example about 40% to about 60% by weight; this means that in step (a) for every 100 kg (on a dry basis) of glyphosate acid in the slurry it is desirable to have about 73 to about 165 kg of water.

Any grade of particulate glyphosate acid can be used. Technical grade glyphosate acid, for example in the form of wet cake having about 8% to about 12% moisture content, has been found to be suitable, but if desired the glyphosate acid can be pre-dried and/or pre-ground. Where an amount or concentration of glyphosate acid or of ammonium glyphosate is specified herein, it is to be understood to exclude moisture that may be present but to include minor amounts or concentrations of impurities. Typically technical grade glyphosate acid wet cake has a glyphosate assay, on a dry basis, of about 95% or higher, indicating that such impurities constitute less than about 5% by weight of technical grade glyphosate acid.

Other materials can optionally be added to or present in the slurry. For example, a small amount of sodium sulfite can be added to inhibit nitrosamine formation. Agitation is required to make and keep the slurry homogeneous; this can be supplied by any suitable means.

Illustratively, a slurry can be made by placing 75 kg water in a tank, and adding, with agitation, 100 kg glyphosate wet cake at 10% moisture content and, if desired, 0.4 kg sodium sulfite.

In the same preferred process of the invention, a base that supplies ammonium cations is then fed into the slurry tank containing the glyphosate acid so as to cause, in step (b), an acid-base reaction forming ammonium glyphosate. Any base that supplies ammonium cations can be used, including ammonium carbonate and ammonium bicarbonate. However, it is generally preferred to use aqueous or anhydrous ammonia. If aqueous ammonia (i.e., ammonium hydroxide) is used, the amount of water supplied by the aqueous ammonia further dilutes the slurry. Typically aqueous ammonia contains about 29% by weight ammonia and can therefore be considered to supply about 71% of its weight as water. This should be factored into the calculation of the amount of water to be used in making the glyphosate acid slurry. Anhydrous ammonia can be supplied in the liquid or gaseous state.

Although the mixing and reaction steps (a) and (b) respectively are described herein for convenience and clarity as separate steps, it will be recognized by those of skill in the art that the acid-base reaction commences as soon as the first portion of acid and base come together in the aqueous reaction medium. Indeed, the reaction can already be substantially completed by the time addition of the base to the slurry is completed.

Preferably aqueous or anhydrous ammonia is added in an approximately stoichiometric amount to result in the formation of monoammonium glyphosate. If less than 1 mole equivalent of ammonia is added per mole of glyphosate acid, a fraction of the glyphosate acid will remain unneutralized. If this fraction is small, for example less than about 20%, resulting in the presence of at least about 4 moles of ammonium glyphosate per mole of unneutralized glyphosate acid, it is generally not unacceptable.

On the other hand, if more than 1 mole equivalent of ammonia is added per mole of glyphosate acid, a fraction of the glyphosate can be considered to be present in the form of the diammonium salt. Subsequent drying of the reaction product will, in such a situation, tend to lead to volatilization of ammonia. For this reason the amount of ammonia added in step (a) should be kept below about 1.25 mole equivalents per mole of glyphosate acid. However, it is preferred that about 0.95 to about 1.05 mole equivalents of ammonia are added per mole of glyphosate acid.

The reaction of ammonia with glyphosate acid is exothermic. Continued agitation of the slurry in step (b) is important to provide efficient heat transfer as well as to ensure a complete and uniform reaction. With conversion of glyphosate acid to ammonium glyphosate, the glyphosate becomes solubilized in the water. The product of the reaction step therefore comprises a concentrated aqueous solution of ammonium glyphosate. A "concentrated" aqueous solution of ammonium glyphosate herein means a solution containing at least about 20%, preferably at least about 40%, and more preferably at least about 55%, by weight of ammonium glyphosate. The upper limit is the limit of solubility of ammonium glyphosate in water, which is temperature dependent.

While the reaction product comprises such a concentrated aqueous solution, it can also contain undissolved solid particles, in which case the reaction product is more accurately described as a slurry. Such undissolved solid particles can be of ammonium glyphosate or of unneutralized glyphosate acid.

It is preferred to maintain the reaction product at an elevated temperature, for example about 65° C. to about 85° C., for maximum solubility of the ammonium glyphosate.

The next step of the process, i.e., step (c) as defined above, comprises drying this reaction product. Any known method of drying a slurry or concentrated solution can be used;

however it has been found, as illustrated by Example 1 herein, that drying can advantageously be performed by contact of the reaction product with a heated surface to form, primarily by evaporation of water, a solid deposit on the heated surface. Drying methods other than those involving contact with a heated surface, for example flash drying and spray drying methods and modifications thereof, have generally produced unsatisfactory results in terms of process efficiency.

The heated surface is preferably the surface of a cylinder such as a drum or roller, and is preferably a metallic surface providing good heat conductivity while being not subject to corrosion in contact with the reaction product of step (b). Suitable metallic surfaces are provided, for example, by stainless steel or chromium plate. In the case of a cylinder, heat is preferably provided to the surface from a heat source or vector in the interior of the cylinder. Superheated steam has been found to be a suitable heat vector. The temperature of the heated surface can be controlled by adjusting the pressure under which the superheated steam is supplied to the cylinder; pressures from about 250 to about 1000 kPa can illustratively be applied, but preferably the steam pressure is about 500 to about 900 kPa. Higher steam pressures within these ranges, generating higher surface temperatures, tend to lead to faster and more complete drying. Temperatures should not be so high, nor residence time of the solid deposit on the heated surface so long, that the glyphosate undergoes thermal decomposition, a process that occurs at 200–230° C. as described by J. E. Franz et al. in American Chemical Society Monograph 189, *Glyphosate: A Unique Global Herbicide,* 1997, pp. 27 and 244. Some volatilization of ammonia can be expected during the drying step, but provided temperature of the heated surface is not excessive and residence time is not too long, such volatilization is generally minimal and presents no problems.

Where the drying step involves atomization of the reaction product in a heated gaseous medium, as in flash drying or spray drying, the resulting solid is automatically recovered in a particulate form. However, in the case of contact drying as described immediately above, a solid deposit forms on the heated surface and this has to be recovered for example by scraping the deposit off the surface. Typically such a scraping action breaks the solid into a particulate form such as flakes, coarse powder or granules, or individual crystals. When the drying step is performed efficiently the moisture content of the particulate solid is typically below about 3% by weight and is preferably below about 1.5%, more preferably below about 1%, by weight.

It will be clear to those of skill in the art from the above description that the type of apparatus known as a drum dryer or roller dryer can provide the requisite heated surface for step (c) of the present process. It will also be clear that other types of apparatus having a heated surface can likewise be suitable. The following description of the use of a drum or roller dryer apparatus in performing step (c) of the process is not to be construed as limiting the invention to use of such apparatus for performing this process step. Drum or roller dryers are described, for example, in *Encyclopedia of Chemical Processing and Design,* Ed. J. J. McKetta, Vol. 17, Pub. Marcel Dekker, Inc., 1983, pp. 17–19; in *Ullmann's Encyclopedia of Industrial Chemistry,* 5th Edition, Vol. B2, Pub. VCH, 1988, pp. 4.25–4.27; and in *Kirk-Othmer Encyclopedia of Chemical Technology,* 4th Edition, Vol. 8, Pub. John Wiley & Sons, 1993, pp. 512–514. Other designs of contact dryers that can be substituted if desired are described in these publications.

Drum dryers can have a single rotating heated drum or, more suitably for the present process, two parallel heated drums that rotate in contrary senses, one clockwise and the other counterclockwise. The axis of rotation is normally horizontal or very nearly horizontal. In operation the surfaces of the parallel drums are separated from each other by a very narrow, generally adjustable, gap known as the "nip". The width of the gap, known as "drum clearance", at the nip is typically set at about 2 to about 10 mm, preferably about 3 to about 7 mm. Preferably the drums rotate in such a way that the surfaces converge above the nip, thereby feeding any material deposited on either or both surfaces into the nip.

In performing step (c) of the present process in such a drum dryer, the reaction product of step (b) is fed on to the converging surfaces of the parallel drums. Feeding of the reaction product can be by spraying, but greater efficiency is generally obtained by permitting the reaction product to flow from a pipe, the tip of which swings like a pendulum over the converging surfaces of the drums and over the nip. Rotational speed of the drums and temperature of the surfaces are controlled so as to permit evaporation of most of the water in the reaction product above the nip. Further drying takes place in and below the nip, resulting in a thin, more or less continuous, solid deposit that adheres to the surfaces of both drums. It has been found that the process operates most efficiently when drying above the nip is such as to result in accumulation of a thick mash in the nip.

In a typical drum dryer, a stationary scraper blade is disposed parallel to the axis of each drum, a scraping edge of the blade contacting the surface of the drum. The blade is angled so that the scraping edge is oriented against the rotational movement of the drum surface. As the drum surface moves against the scraping edge of the blade, any solid deposit thereon is removed from the surface and falls or is transported to a hopper or other collecting vessel. Typically during scraping the solid material breaks into small flakes.

Precise location of the scraper blades relative to the nip of the drums is not critical, but it is generally desired for maximum drying to permit a fairly long period of contact of the solid deposit with the heated surfaces of the drums, and for this reason a suitable placement for the scaper blade for each drum is approximately diametrically opposite the nip, i.e., about 180° from the nip in the sense of rotation of the drum, or slightly above that location. A typical placement is about 180° to about 220°, for example about 200°, from the nip.

The flakes of solid material produced by scraping the solid deposit off the heated surface can constitute the particulate solid material that proceeds to step (d) of the present process. However, such flakes tend to give rise to low bulk density and are often not efficiently processed in step (d). For this reason, it is preferred after recovery of the dried material to grind the flakes to form the particulate solid material to be used in step (d). Such an optional grinding step is herein referred to as "pre-grinding" to distinguish it from the further size reduction that occurs in step (d).

Pre-grinding can be performed in any suitable apparatus, nonlimiting examples being mechanical grinders such as a pin mill or a hammer mill. Particle size of pre-ground material is not critical so long as the material is suitable for feeding to the apparatus described below for step (d).

The step of forming ammonium glyphosate powder having mean particle size of about 5 to about 20 $\mu$m, i.e., step (d) of the process of the invention as defined above, is the aspect of the process that requires most careful attention. It has surprisingly been found that, of all the types of apparatus known in the art for particle size reduction to below about 20 μm, most are unsuitable in the present process, for reasons of process efficiency, product quality for downstream formulation, or both. It has been found unexpectedly critical to use an apparatus in which the particulate solid from step (c) is accelerated in a turbulent high-velocity gas stream, wherein ammonium glyphosate powder of the desired particle size is generated primarily by particle-particle attrition.

A suitable apparatus is a fluid energy mill or jet mill as described, for example, in *Encyclopedia of Chemical Processing and Design*, Ed. J. J. McKetta, Vol. 50, Pub. Marcel Dekker, Inc., 1995, pp. 433–435; in *Ullmann's Encyclopedia of Industrial Chemistry*, 5th Edition, Vol. B2, Pub. VCH, 1988, pp. 5.33–5.35; in *Kirk-Othmer Encyclopedia of Chemical Technology*, 4th Edition, Vol. 22, Pub. John Wiley & Sons, 1997, pp. 291–293; and in *Perry's Chemical Engineer's Handbook*, 7th Edition, Pub. McGraw-Hill, 1997, pp. 20.47–20.48. Such apparatus is to be distinguished from a mechanical mill wherein comminution of particles occurs primarily by impact of hammer or beater elements or pins. Some mechanical mills have integral air classifiers, in which air flow is used to segregate particles of different sizes; however in such mills, sometimes called air classifying mills, particle-particle attrition that occurs in the air flow is secondary to mechanical impact in reducing particle size. Air classifying mills have not been found suitable for use in step (d) of the present process, although they can be used for a pre-grinding operation as outlined above.

In fluid energy or jet milling, the ultimate particle size achieved depends on initial particle size and on residence time in the mill, the latter depending in turn upon feed rate. The smaller the initial particle size, the greater is the feed rate at which the mill can be operated to produce finished particles of a given mean size. As fluid energy mills have much higher energy consumption than mechanical impact mills, it is generally more economical to pre-grind in a mechanical impact mill as described above, and complete the size reduction operation in the fluid energy mill.

The turbulent high-velocity gas stream in the fluid energy or jet milling operation can be a stream of air, or alternatively nitrogen or another gas. Good results have been obtained using air, supplied at a pressure of about 100 psig (690 kPa).

Within the ultimate size range of about 5 to about 20 μm specified herein, the smaller the particle size the more suitable is the ammonium glyphosate powder for downstream formulation. This is probably due in part to the progressive increase in surface area available for adsorption of surfactant as mean particle size becomes smaller. Preferably, therefore, the ammonium glyphosate powder produced in step (d) of the present process has a mean-particle size of about 5 to about 15 μm, more preferably about 5 to about 10 μm. Alternatively, the ammonium glyphosate powder produced in step (d) preferably has a specific surface area of about 1.25 to about 3 $m^2/g$, more preferably about 1.5 to about 3 $m^2/\mu g$. Ideally, the ammonium glyphosate powder produced in step (d) has a mean particle size of about 5 to about 7 μm and a specific surface area of about 2.25 to about 3 $m^2/g$.

It should be noted, however, that while small particle size, probably through the attendant large surface area, appears to be a necessary condition for good downstream processability as described herein, it is not a sufficient condition. Particles within the requisite size range have been made, for example by drum drying followed by mechanical impact milling, that have been found unsuitable for downstream formulation. It is not at present understood why particles formed primarily by particle-particle impact, as in a fluid energy or jet mill, should have more suitable properties for downstream formulation than similarly sized particles formed by other means.

An embodiment of the present invention provides a process wherein ammonium glyphosate powder prepared by steps (a) to (d) is further processed with surfactant to make a granular formulation by steps (e) to (g) and optionally step (h) as defined above. These steps (e) to (h) are known in the art, but have not previously been successfully applied to an ammonium glyphosate powder produced by a process involving reaction of glyphosate acid and ammonia in an aqueous slurry. It appears that the use in step (d) of a turbulent high-velocity gas stream to effect particle size reduction is the key to enabling ammonium glyphosate from a slurry process to be produced efficiently and economically in a form suitable for further processing via steps (e) to (g) and optionally (h).

In the first step of the downstream formulation process, i.e., step (e) of a process of the present invention, ammonium glyphosate powder produced by steps (a) to (d) are mixed in an amount of about 75 to about 85 parts by weight with about 15 to about 25 parts by weight of one or more surfactants, and with about 3 to about 10 parts by weight of water per 100 parts by weight of ingredients other than water, to form an extrudable wet mix having a weight ratio of total surfactant to ammonium glyphosate of about 1:9 to about 1:3. The surfactant typically helps to condition the paste to form an extrudable wet mix; however, a major function of the surfactant is to enhance herbicidal efficacy of the finished product. The surfactant component can consist of a single type of surfactant, or it can comprise two or more surfactant materials. Where two or more surfactant materials are used, they can be added individually to the ammonium glyphosate or they can be first blended together and then added in mixture. Other materials, including water and/or glycols, can optionally be admixed with the surfactant or surfactants prior to addition to the ammonium glyphosate.

Any class of surfactant can be used; however, it is generally preferred that at least one surfactant added in step (b) is cationic or amphoteric. An exception is the class of surfactants known as alkyl polyglycosides (APGs), which are nonionic but which are also among preferred surfactants for use in the present invention. Among illustrative classes of cationic and amphoteric surfactants useful in the invention are alkylamines, alkylammonium salts, alkylamine oxides, alkylbetaines, alkyletheramines, alkyletherammonium salts and alkyletheramine oxides. Polyoxyethylene derivatives of such cationic and amphoteric surfactants are particularly preferred. The term "alkyl" is used in the present context to denote one or more linear or branched, saturated or unsaturated hydrocarbyl chains having about 8 to about 22 carbon atoms.

This mixing can be done in any suitable vessel such as a kneader. If more than one surfactant is to be included, the surfactants can be pre-blended. The surfactant or surfactant blend is preferably added in a liquid state; even in the case of a liquid surfactant it is generally helpful to heat the surfactant to bring it into a readily flowable condition before adding it to the ammonium glyphosate. Solid surfactants can be added in the solid state or alternatively can be heated to a temperature above their melting point and added in the liquid state. Preferred surfactants are those that are individually liquid or in a flowable state, in the absence of water or other solvent, at 25° C.

The amount of water added in step (e) is important. There is an optimum range for amount of water added that varies depending on the absorption and/or adsorption characteristics of the ammonium glyphosate powder. For a powder having very favorable absorption and/or adsorption characteristics, the optimum range can be as wide as from about 3 to about 10 parts by weight of water per 100 parts by weight of ingredients other than water. Above this optimum range, the resulting wet mix tends to become sticky, with the result that upon extrusion the extrudate or granules formed therefrom tend to agglomerate. Below the optimum range, the mix tends to be difficult to extrude and the extrudate or granules formed therefrom tend to be excessively friable.

If the powder has less favorable absorption and/or adsorption characteristics, the optimum range for amount of water added is typically narrower; in particular the upper limit of the optimum range is lower. If the powder is intolerant of any amount of water in excess of about 5 parts by weight per 100 parts by weight of ingredients other than water, it is generally unsuitable for downstream formulation by an extrusion granulation process as described herein.

In step (e), mixing is continued until a homogeneous wet mix, preferably having a dough-like consistency, is obtained. Ingredients other than those mentioned above can be added if desired during the mixing step.

The next step, i.e., step (f) of a process of the present invention as defined above, is a granulating step that comprises extruding the wet mix to form extrudate strands that break to form moist coherent granules. Extrusion is preferably carried out using a low-pressure radial or twin-dome extruder. The wet mix is extruded through screens having apertures preferably of diameter about 0.5 to about 2 mm, more preferably about 0.6 to about 1.2 mm. The extrudate emerging from the screens initially forms elongated strands which tend to break spontaneously to form short cylindrical granules. If the strands do not break readily it may be necessary to add a cutting device at the extruder head; however, if the ammonium glyphosate powder has the desired absorption and/or adsorption properties and the amount of water added is within the optimum range as described above, a cutting operation is usually not necessary.

Immediately after extrusion, the granules are moist and coherent, but are not sticky and do not agglomerate. At this point the granules can, if desired, be subjected to a rolling or tumbling action, for example in a tumbler or spheronizer, to give them a more rounded shape and to make them more uniform in size.

The next step, i.e., step (g) of a process of the present invention as defined above, involves drying the granules. Any known drying method can be used, but a preferred method is fluid bed drying. The granules are preferably dried to a moisture content below about 1%, more preferably below about 0.5%, by weight.

At this point the dried granules can be packaged, but it is generally preferred to classify the granules, for example by sieving, to retain only those in a desired size range. This is optional step (h) of a process of the present invention as defined above. An illustrative size range to be retained is larger than 40 mesh (about 0.6 mm) and smaller than 5 mesh (about 5 mm). Over- and under-sized granules or fragments or aggregates thereof can be recycled by adding them to the wet mix prior to extrusion.

EXAMPLES

The following Examples are provided for illustrative purposes only and are not intended to limit the scope of the present invention. The Examples will permit better understanding of the invention and perception of its advantages and certain variations of execution.

Example 1

In a program of evaluation of drying methods for a concentrated ammonium glyphosate solution such as is produced by reacting glyphosate acid with aqueous or anhydrous ammonia in a slurry, the following systems and apparatus were tested:

A. Flash drying in a Pulvocron™ PC-20 air classifying mill (Hosokawa Bepex Corp., Minneapolis, Minn.).

B. Spray drying in a UnisonTM (Hosokawa Bepex Corp., Minneapolis, Minn.) spray dryer.

C. Spray drying in a spray dryer (APV Anhydro, Copenhagen, Denmark).

D. Spray drying in a fluidized bed spray dryer (APV Anhydro, Copenhagen, Denmark).

E. Contact drying with a 24 inch×24 inch (600 mm×600 mm) Buflovak™ atmospheric double drum dryer (Blaw Knox Corp., Buffalo, N.Y.).

A. Flash drying

To simulate the reaction product of a glyphosate acid slurry with ammonia, a 56% by weight ammonium glyphosate solution was prepared by dissolving dry ammonium glyphosate, technical grade (MON 8750 of Monsanto) in water. To ensure dispersion of undissolved solids, drums containing the ammonium glyphosate solution were agitated on a drum roller for about 90 minutes prior to the flash drying tests.

The liquid ammonium glyphosate solution was fed to a Pulvocron™ PC-20 by a Moyno pump at feed rates ranging from 63.5 to 204 kg/h in individual tests. In the Pulvocron the liquid was met by air heated to a temperature ranging from 89° C. to 268° C. at an air flow rate ranging from 23 to 36 $m^3$/minute in individual tests. Beater plates in the Pulvocron threw the liquid against a segmented liner while the hot air flashed off the water. Various combinations of beater plates were installed in individual tests.

In all tests, build-up of dried solid material occurred on the walls and beater plates of the Pulvocron, eventually plugging the system and preventing discharge of dry product. No improvement was noted even with removal of the air classifier from the Pulvocron in an effort to improve discharge. Back-mixing of already dried material with the liquid feed also did not help.

B. Spray drying with Unison dryer

In prior tests with conventional spray dryers fitted with centrifugal atomizers, the liquid was sprayed towards the walls of the spray drying chamber, where dried material accumulated. None of the dried material was discharged. By contrast, the Unison™ spray dryer uses a pulsed combustion system to provide a sonic wave that atomizes a liquid feed. This atomization results in a more gentle release of the liquid feed into the chamber, with less tendency for contact with and therefore adhesion of dried material to the walls.

The dryer tested had a spray drying chamber having an upper cylindrical section of diameter 1.8 m and height 4.3 m, and a lower 70° conical section of height 2.1 m. Heated air and liquid feed were introduced at the top of the chamber and air and dried product discharged through a 300 mm diameter duct at the bottom. Dried product was fed to a cyclone separator and baghouse for collection.

As feed liquids for testing this system, ammonium glyphosate solutions were prepared by dissolving MON 8750 in water as for the flash drying test above. A 50% by weight ammonium glyphosate solution was prepared for one test, while for other tests aqueous slurries were used containing ammonium glyphosate above its limit of solubility. These slurries contained 60% or 70% total "solids", i.e., including dissolved ammonium glyphosate.

The liquid feed was preheated to 32° C., 66° C. and 74° C. in individual tests. Air temperature was about 255° C. Feed rate was set to 182 kg/h. It was found that the 70% ammonium glyphosate slurry was too viscous to feed efficiently, while the 50% ammonium glyphosate solution, when used as the feed, resulted in rapid build-up of a hard-to-remove glassy material on the chamber walls. It is believed that absence of solid particles in the feed inhibited rapid crystallization of the ammonium glyphosate, resulting in the glassy deposit.

By contrast, the 60% ammonium glyphosate slurry, preheated to 32° C. or 66° C., gave effective spray drying. Yields were 90% and 77% respectively. Some build-up of white powdery material was observed on the walls, particularly in the lower conical section near the discharge outlet, but this was insufficient to adversely affect the spray drying operation. Moisture content of the product ranged from 1.4% to 1.7% by weight.

In a repeat test using 60% slurry at 66° C., the discharge outlet became plugged with loose and friable material and the system shut down after 40 minutes.

C. Spray drying with APV spray dryer

The spray dryer tested at APV had a centrifugal atomizer and a built-in air broom to cool and sweep the walls and bottom of the spray drying chamber. The chamber was cylindrical, 3.0 m in diameter and 3.0 m high, with a flat bottom. Liquid feed and air were introduced at the top and dried product discharged at the bottom. Product was fed to a cyclone separator and baghouse for collection.

The liquid feed for all tests of the APV spray dryer was a 60% ammonium glyphosate slurry, prepared exactly as for the Unison test above.

Regardless of feed rate, air temperature and air flow to the air broom, product dried in the APV spray dryer failed to discharge. It was concluded that this apparatus was not suitable for drying ammonium glyphosate.

D. Spray drying with APV fluidized bed spray dryer

The dryer used for these tests had a spray drying chamber having an upper cylindrical section of diameter 1.5 m and height 1.5 m and a lower conical section of height 0.9 m, discharging to a fluidized bed immediately below. Discharge from the fluidized bed was from the bottom via a rotary air lock. Material was fed from the fluidized bed to a cyclone separator, from which fine particles were recycled to the conical section of the drying chamber.

The same 60% ammonium glyphosate slurry was used as in the previous tests above. Air inlet temperature in the spray drying chamber was 215° C. and in the fluidized bed 100° C. About 30 kg ammonium glyphosate powder was added to the fluidized bed to prime the system.

Dried product failed to discharge from the spray drying chamber to the fluidized bed because of accumulation and bridging in the conical section of the chamber. It is believed that design modifications could alleviate this problem; however, from all tests conducted it was concluded that spray drying was not the most appropriate method of converting an ammonium glyphosate solution or slurry to dry powder on a manufacturing scale.

E. Drum drying

E-1: Feasibility test

Before attempting to dry ammonium glyphosate in the 24 inch×24 inch Buflovak™ atmospheric double drum dryer, a feasibility study was conducted using a 6 inch×6 inch (150 mm×150 mm) laboratory model. The dimensions (e.g., 6 inch×6 inch) relate to the diameter and length of each drum. The 6 inch×6 inch laboratory model has a total drum surface area of about 1.57 square feet (0.145 m$^2$), which represents about 6.3% of the surface area of a 24 inch×24 inch model, i.e., about 25 square feet (2.31 m$^2$).

For the feasibility study, a 49% by weight ammonium glyphosate solution was prepared by dissolving MON 8750 in water. When fed to the drum dryer at a temperature of 50° C., the solution was successfully dried to flakes having a moisture content of 1.2%. A production rate of 10.6 kg/m$^2$/h was calculated.

E-2: First scale-up test series

For this series of tests, a 59–60% by weight ammonium glyphosate slurry was prepared by dissolving MON 8750 in water. About 2–5% of the ammonium glyphosate remained undissolved. The slurry was fed to a 24 inch×24 inch double drum dryer at a temperature of 74° C., using a pendulum feed system. Both drums were internally heated using superheated steam, initially at a pressure of 95 psig (656 kPa), and were rotated initially at 3 rpm. In a run of about 10–15 minutes, flakes of dry ammonium glyphosate of good appearance were produced having a moisture content of 1.1%, at a production rate of 28.5 kg/m$^2$/h.

Data for this and other runs, each of about 10–15 minutes, where various parameters were varied, are shown in the table below.

| run no. | 1 | 2 | 3 | 4 | 5 |
|---|---|---|---|---|---|
| % ammonium glyphosate in feed | 59 | 59 | 59 | 60 | 51[1] |
| feed temperature, ° C. | 74 | 69 | 64 | 88[2] | 56 |
| steam pressure, kPa | 656 | 676 | 676 | 869 | 856 |
| rotation speed of drums, rpm | 3.0 | 4.5 | 6.0 | 5.0 | 3.5 |
| drum clearance at nip, mm | 4.6 | 4.3 | 4.3 | 4.4 | 4.6 |
| production rate, kg/m$^2$/h | 28.5 | 43.6 | 35.4 | 42.4 | 30.1 |
| % moisture content of product | 1.1 | 0.6 | 0.9 | 0.7[3] | 0.7 |

[1]at this reduced ammonium glyphosate concentration, feed was a clear solution
[2]at this increased temperature, feed was a clear solution
[3]mean of three samples ranging from 0.5% to 0.9% moisture content Optimum conditions in this test series appeared to be with a 59–60% ammonium glyphosate slurry and a drum rotation speed of about 4.5 to 5 rpm. A longer production run, lasting about 60 minutes, was therefore made using a 60% slurry at a feed temperature of 66° C., 662 kPa steam pressure and 4.5 rpm rotation speed. Drum clearance at the nip was narrowed slightly to 3.0 mm. This run was very successful, giving a product having an average moisture content of about 0.8% at a production rate of 39.5 kg/m$^2$/h.

E-3: Second scale-up test series

Ammonium glyphosate feed for this series of tests was made by preparing an aqueous slurry of glyphosate wet cake and neutralizing stoichiometrically with aqueous ammonia to produce a 58% by weight solution or slurry of ammonium glyphosate. For some tests this feed was slightly diluted with water.

Test runs were made using the 24 inch×24 inch drum dryer as in the previous series. Data are shown in the table below.

| run no. | 1 | 2 | 3 | 4 | 5 | 6 | 7 | 8 |
|---|---|---|---|---|---|---|---|---|
| duration of run, minutes | 15 | 60 | 292 | 15 | 60 | 60 | 175 | 53 |
| % ammonium glyphosate in feed | 58 | 58 | 58 | 54 | 54 | 54 | 56 | 56 |
| feed temperature, °C. | 96 | 96 | 84 | 63 | 63 | 63 | 82 | 83 |
| steam pressure, kPa | 662 | 718 | 745 | 759 | 704 | 718 | 828 | 828 |
| rotation speed of drums, rpm | 4.3 | 4.5 | 4.5 | 4.3 | 4.3 | 4.0 | 4.0 | 3.0 |
| drum clearance at nip, mm | 3.3 | 4.3 | 4.0 | 3.3 | 3.0 | 3.0 | 3.0 | 7.3 |
| production rate, kg/m²/h | 34.0 | 38.6 | 38.8 | 32.6 | 31.9 | 30.5 | 35.4 | 43.2 |
| % moisture content of product | 1.8 | 1.2 | 1.4 | 1.6 | 1.4 | 1.4 | 0.9 | 2.0 |

E-4: Third scale-up test series

Ammonium glyphosate feed for this series of tests was made as for the previous series but at lower concentration and at three levels of neutralization: stoichiometric (i.e., 100% neutralization with ammonia), 102% and 104%.

Test runs were made using the 24 inch×24 inch drum dryer as in the previous series. Data are shown in the tables below (n.r.=not recorded).

| run no. | 1 | 2 | 3 | 4 | 5 | 6 | 7 |
|---|---|---|---|---|---|---|---|
| duration of run, minutes | 30 | 20 | 15 | 15 | 15 | 15 | 20 |
| % ammonium glyphosate in feed | 45 | 45 | 45 | 45 | 45 | 45 | 45 |
| degree of neutralization, % | 100 | 100 | 100 | 102 | 102 | 102 | 102 |
| feed temperature, °C. | 82 | 83 | 82 | 97 | n.r. | 84 | 81 |
| steam pressure, kPa | 518 | 690 | 814 | 414 | 518 | 690 | 828 |
| rotation speed of drums, rpm | 5.0 | 5.0 | 5.0 | 5.0 | 5.0 | 5.0 | 5.0 |
| drum clearance at nip, mm | 2.7 | 5.2 | 6.7 | 3.0 | 3.0 | 3.3 | 3.6 |
| production rate, kg/m²/h | 31.6 | 47.7 | 52.1 | 23.6 | 37.7 | 38.5 | 42.0 |
| % moisture content of product | 2.1 | 1.8 | 1.3 | 3.4 | 2.0 | 1.2 | 1.0 |

| run no. | 8 | 9 | 10 | 11 | 12 | 13 | 14 | 15 |
|---|---|---|---|---|---|---|---|---|
| duration of run, minutes | 10 | 10 | 10 | 10 | 10 | 20 | 70 | 78 |
| % ammonium glyphosate in feed | 45 | 45 | 45 | 45 | 45 | 45 | 45 | 45 |
| degree of neutralization, % | 104 | 104 | 104 | 104 | 104 | 104 | 104 | 102 |
| feed temperature, °C. | 80 | 89 | 88 | 86 | 86 | 80 | 83 | 82 |
| steam pressure, kPa | 414 | 414 | 518 | 690 | 807 | 821 | 690 | 690 |
| rotation speed of drums, rpm | 3.0 | 5.0 | 5.0 | 5.0 | 5.0 | 3.0 | 5.0 | 5.0 |
| drum clearance at nip, mm | 3.3 | 3.3 | 3.6 | 3.3 | 5.2 | 5.5 | 3.3 | 3.3 |
| production rate, kg/m²/h | 19.5 | 26.5 | 34.2 | 33.6 | 30.1 | 35.7 | 34.0 | 37.8 |
| % moisture content of product | 2.0 | 2.3 | 1.4 | 0.9 | 0.9 | 0.5 | 1.4 | 1.1 |

E-5: Fourth scale-up test series

Ammonium glyphosate feed for this series of tests was made by preparing an aqueous slurry of glyphosate wet cake and neutralizing stoichiometrically with aqueous ammonia to produce solutions or slurries of ammonium glyphosate at various concentrations.

Test runs were made using the 24 inch×24 inch drum dryer as in the previous series. Data are shown in the table below (n.r.=not recorded).

| run no. | 1 | 2 | 3 | 4 | 5 | 6 |
|---|---|---|---|---|---|---|
| duration of run, minutes | 104 | 99 | 140 | 134 | 140 | 129 |
| % ammonium glyphosate in feed | 53 | n.r. | 47 | 59–64 | 57 | 59 |
| feed temperature, °C. | 77 | 82 | 74 | 81 | 79 | 79 |
| steam pressure, kPa | 814 | 821 | 814 | 828 | 828 | 828 |
| rotation speed of drums, rpm | 4.0 | 5.0 | 4.0 | 4.0 | 4.0 | 4.0 |
| drum clearance at nip, mm | 4.9 | 5.5 | 5.5 | 5.5 | 4.6–7.0 | 5.5 |
| production rate, kg/m²/h | 47.7 | 54.8 | 45.4 | 45.7 | 46.2 | 52.1 |
| % moisture content of product | 1.6 | 1.3 | 1.5 | 1.2 | 1.6 | 1.2 |

From the tests described in Example 1 herein, it is clear that drum drying is an acceptable drying method for a concentrated ammonium glyphosate solution prepared by reacting glyphosate acid and ammonia in an aqueous slurry. Further optimization of the drying process can readily be performed by one of skill in the art by routine testing.

It has been found that neither the immediate product of a spray drying step nor that of a drum drying step is directly suitable for downstream processing by extrusion granulation to make a surfactant-containing dry formulation. The particulate ammonium glyphosate generated, whether by spray drying or by contact drying on a heated surface, generally lacks the absorption and/or adsorption properties necessary for such downstream processing to result in a granular product of the required quality. In other words, proceeding directly from step (c) to step (e) as defined herein is not likely to give satisfactory results. Step (d), the size reduction step, is essential to the process of the present invention.

Example 2

A program of evaluation of size reduction methods for step (d) was undertaken as set out below. First, a test procedure was developed to evaluate suitability of the products of various size reduction methods for downstream formulation with surfactant via an extrusion granulation process. The procedure used the following laboratory-scale apparatus:

Fuji Paudal KDHJ-60 kneader
Fuji Paudal EXDCS-60 extruder
Aeromatics STREA fluid bed dryer The procedure was adapted for two formulations. Formulation A has the following composition on a 100% dry basis:

| | |
|---|---|
| ammonium glyphosate (MON 8750) | 80% |
| polyoxyethylene (20) tallowamine | 20% | while Formulation B has the following composition on a 100% dry basis:

| | |
|---|---|
| ammonium glyphosate (MON 8750) | 75% |
| polyoxyethylene (15) N-methylstearylammonium chloride | 10% |
| polyoxyethylene (10) dodecylphenol | 10% |
| polyethylene glycol, average MW 8000 | 5% |

The principle of the procedure is that a sample of particulate ammonium glyphosate having favorable qualities for extrusion granulation with surfactant tolerates addition of a greater amount of water to the extrudable wet mix without causing the extrudate to become excessively sticky, by comparison with a sample having unfavorable qualities. A sample that tolerates addition, for example, of 10 parts by weight of water per 100 parts by weight of ingredients other than water (an amount referred to herein as "10% water"), is much more suitable for extrusion granulation than one that tolerates only 5 parts by weight of water per 100 parts by weight of ingredients other than water ("5% water").

The procedure for Formulation A was as follows.

1. Particulate ammonium glyphosate, 16 kg, was added to the kneader.
2. The water jacket of the kneader was brought to a temperature of 75° C. by circulation of hot water in the jacket.
3. Polyoxyethylene (20) tallowamine surfactant, 4 kg, was heated to 60–80° C. in a microwave oven.
4. The kneader was turned on and the heated surfactant was poured slowly (over a period of 30–60 seconds) over the particulate ammonium glyphosate.
5. Lukewarm water, 1 liter (5%), was slowly poured into the mixture of ammonium glyphosate and surfactant.
6. The kneader was operated for a further 10 minutes, maintaining jacket temperature at 75° C., to produce a dough-like wet mix.
7. The wet mix was removed from the kneader and fed to the extruder, set to run at the "0.5" speed and with a 1 mm screen installed in the extrusion head.
8. A small quantity of the wet mix was allowed to extrude to establish a steady state and the extrudate thus formed was returned to the kneader.
9. About 1–2 kg of wet mix was extruded.
10. The appearance of the extrudate was noted. In particular, any tendency for the strands of extrudate to break spontaneously into segments (a desirable property) as opposed to remaining as long "stringy" noodles was recorded, as was any tendency of the strands to stick together or to aggregate to form lumps that did not readily separate (an undesirable property).
11. The extrudate was transferred to the fluid bed dryer and dried at 70° C. for 20 minutes.
12. The resulting granules were screened to remove oversized (5 mesh) and undersized (40 mesh) material. A tactile evaluation of the granules was performed to determine if the granules were hard and coherent (desirable), soft and friable (undesirable) or sticky or moist to the touch due to the presence of unabsorbed and/or unadsorbed surfactant (undesirable).
13. The above procedure was repeated, except that the amount of water added was increased by 0.2 liter (1%) for each repetition, up to a maximum of 2 liters (10%).
14. If acceptable extrusion granulation, as determined by appearance of the moist extrudate and of the dried granules, occurred at any level of water addition from 5% to 10%, the properties of the ammonium glyphosate were deemed to be suitable for downstream processing to make Formulation A. If no acceptable extrusion granulation occurred at any level of water addition from 5% to 10%, the properties of the ammonium glyphosate were deemed to be unsuitable.

For Formulation B, the procedure was similar, except for steps 1–6 which were as follows.

1. Particulate ammonium glyphosate, 15 kg, was added to the kneader.
2. The water jacket of the kneader was kept at ambient temperature.
3. A blend of 2 kg polyoxyethylene (15) N-methyl stearylammonium chloride surfactant (Ethoquad™ 18/25 of Akzo), 2 kg polyoxyethylene (10) dodecylphenol (Rexol™ 65/10 of Huntsman) and 1 kg polyethylene glycol, average molecular weight 8000, was heated to 55–65° C. in a microwave oven. The blend was stirred to ensure thorough mixing of the ingredients.
4. The kneader was turned on and the heated blend was poured slowly (over a period of 30–60 seconds) over the particulate ammonium glyphosate.
5. Lukewarm water, 1 liter (5%), was slowly poured into the mixture of ammonium glyphosate and surfactant.
6. The kneader was operated for a further 5 minutes, maintaining jacket at ambient temperature, to produce a dough-like wet mix.

In a program of evaluation of size reduction methods following drum drying of ammonium glyphosate produced by reacting glyphosate acid with aqueous or anhydrous ammonia in a slurry, the following systems and apparatus were tested:

A. Milling in a Mikro-ACM™ Pulverizer Model 10 air classifying mill (Micron Powder Systems, Summit, N.J.).

B. Milling in a Powderizer™ NSP 2 air classifying mill with and without pre-grinding using a Simpactor™ pin mill (Sturtevant, Boston, Mass.).

C. Milling in a Strong-Scott Pulvocron™ PC-20 air classifying mill (Hosokawa Bepex Corp., Minneapolis, Minn.) with and without pre-grinding using a Commander™ Model 2400 hammer mill (Jacobson Inc., Minneapolis, Minn.).

D. Milling in a Schutz-O'Neill Model 22H air classifying mill following pre-grinding using a Commander™ hammer mill (Jacobson Inc., Minneapolis, Minn.).

E. Milling in a Prema™ Model CLM35 air classifying mill (Prater Industries, Chicago, Ill.).

F. Milling in a Rotormill™ Model 3000 (International Process Equipment Co., Pennsauken, N.J.).

G. Milling in a Micronizer™ jet mill with and without pre-grinding in a Simpactor™ pin mill (Sturtevant, Boston, Mass.).

In each case where the size reduction equipment was successfully operated to provide a fine particulate ammonium glyphosate product, the product was characterized by its suitability for downstream processing to make Formulation A and/or Formulation B by the procedures described in Example 2 above. Products were also characterized by measurement of average particle size, with a Brinkman™ Model 2010 or a Coulter™ Ls 130 particle size analyzer with a Micro-Volume Module, using 2-propanol as the dispersing medium. Products were further characterized by measurement of specific surface area with a Digisorb™ 2500 B.E.T. analyzer using krypton as the adsorbed gas.

A. Mikro-ACM™ air classifying mill

The Mikro-ACM™ Model 10 Pulverizer of Micron Powder Systems is an air classifying mill having a bar-type rotor with an integrally mounted, separately driven classifier wheel. For the present tests the equipment was fitted either with a four-bar hammer rotor or with a pin rotor. The classifier wheel was either a 24 long blade type or a 24 blade 30° canted type separator. The liner inside the mill was either a multi-deflectional type or a smooth ceramic type. The feed to the mill was drum dried ammonium glyphosate in the form of 2–5 cm flakes having a moisture content of 1% by weight and a bulk density of 323 kg/m$^3$.

In a series of ten runs, a number of parameters were varied including rotor type, rotor speed (3500 or 7000 rpm), liner type, classifier wheel type, classifier wheel rotation speed (700–3500 rpm), air flow (11.2–19.6 m$^3$/minute), feed rate (23–305 kg/h) and feed temperature (ambient, i.e., 21–24° C., or cooled to 14° C.). Significant build-up of product was observed inside the mill in all runs using the multi-deflectional liner. However, in two of these runs a sufficient quantity of powder was obtained to warrant characterization. Build-up was avoided when the smooth ceramic liner was installed and rotor speed was reduced. Data are presented in the tables below (n.t.=not tested).

| run no. | 1 | 2 | 3 | 4 | 5 |
|---|---|---|---|---|---|
| duration of run, minutes | 117 | 15 | 9 | 7 | 16 |
| rotor type | hammer | hammer | hammer | pin | pin |
| rotor speed, rpm | 7000 | 7000 | 7000 | 7000 | 7000 |
| liner type[1] | md | md | md | md | md |
| classifier wheel type[2] | canted | canted | long | long | long |
| classifier wheel speed, rpm | 3500 | 3500 | 3500 | 3500 | 3500 |
| air flow, m$^3$/minute | 11.2 | 19.6 | 19.6 | 19.6 | 19.6 |
| feed rate, kg/h | 23 | 88 | 63 | 109 | 155 |
| feed temperature, °C. | 24 | 24 | 24 | 21 | 21 |
| unacceptable build-up? | yes | yes | yes | yes | yes |
| product characterization: | | | | | |
| particle size[3], μm | 8.6 | n.t. | n.t. | n.t. | 16.3 |
| specific surface area, cm$^2$/g | 1.80 | n.t. | n.t. | n.t. | n.t. |
| suitability for extrusion: | | | | | |
| Formulation A | n.t. | n.t. | n.t. | n.t. | n.t. |
| Formulation B | excellent | n.t. | n.t. | n.t. | excellent |

| run no. | 6 | 7 | 8 | 9 | 10 |
|---|---|---|---|---|---|
| duration of run, minutes | 11 | 10 | 5 | 9 | 7 |
| rotor type | pin | hammer | hammer | pin | pin |
| rotor speed, rpm | 7000 | 7000 | 7000 | 7000 | 3500 |
| liner type[1] | md | md | md | md | ceramic |
| classifier wheel type[2] | long | long | canted | long | long |
| classifier wheel speed, rpm | 700 | 700 | 3500 | 1500 | 3500 |
| air flow, m$^3$/minute | 19.6 | 19.6 | 19.6 | 19.6 | 19.6 |
| feed rate, kg/h | 258 | 305 | 89 | 293 | 117 |
| feed temperature, °C. | 24 | 24 | 14 | 24 | 24 |
| unacceptable build-up? | yes | yes | yes | yes | no |
| product characterization: | | | | | |
| particle size[3], μm | 54.8 | n.t. | n.t. | 31.2 | 45.1 |
| specific surface area, cm$^2$/g | n.t. | n.t. | n.t. | 0.70 | n.t. |
| suitability for extrusion: | | | | | |
| Formulation A | n.t. | n.t. | n.t. | n.t. | n.t. |
| Formulation B | no good | n.t. | n.t. | borderline | no good |

[1]md = multi-deflectional type
[2]long = 24 long blade type; canted = 24 blade 30° canted type
[3]Brinkman Only in run no. 10, with installation of the smooth ceramic liner, did the Mikro-ACM™ air classifying mill operate acceptably, but average particle size (45.1 μm) of the resulting powder was in that case relatively large and was found to be unsuitable for downstream formulation by the extrusion process. For this reason, the Mikro-ACM™ air classifying mill was judged to be an unsatisfactory apparatus for the size reduction step of the present process.

B. Powderizer™ NSP 2 air classifying mill

The Powderizer™ NSP 2 of Sturtevant is an air classifying mill similar in many respects to the Mikro-ACM™ but having different internal geometry and air flow pattern. The rotor is fitted with hammers. The Simpactor™ of Sturtevant is a pin mill having a rotor carrying one or two peripheral rows of pins which pass between stationary pins as the rotor spins. Material to be ground is fed near the axis of the rotor and passes between the rotor pins and stationary pins before being discharged at the periphery. The pin mill was used for pre-grinding flakes of drum dried ammonium glyphosate prior to milling in the Powderizer™ air classifying mill. In some runs of the Powderizer™, the ammonium glyphosate was fed directly in the form of flakes, as in the Mikro-ACM™ test above.

In a series of eight runs, a number of parameters were varied including classifier wheel type (short cage or long cage), classifier wheel rotation speed (2000–3800 rpm) and feed rate (126–554 kg/h). Rotor speed was kept constant at 5150 rpm. Significant build-up of product was observed on the classifier wheel. Where the Simpactor™ pin mill was used for pre-grinding, it was operated at 3600 rpm with a feed rate of 1452 kg/h. Data are presented in the tables below (n.t.=not tested).

| run no. | 1 | 2[1] | 3 | 4 |
|---|---|---|---|---|
| duration of run, minutes | 4 | | 15 | 9 |
| classifier wheel type | short cage | long cage | long cage | long cage |
| classifier wheel speed, rpm | 3800 | 3800 | 3800 | 3800 |
| feed pre-ground? | no | no | no | no |
| feed rate, kg/h | 445 | | 126 | 191 |
| unacceptable build-up? | yes | | yes | yes |
| product characterization: | | | | |
| particle size[2], μm | 15.8 | n.t. | 10.4 | 10.2 |
| specific surface area, cm$^2$/g | 1.22 | n.t. | 1.72 | 1.62 |

-continued

| run no. | 1 | 2[1] | 3 | 4 |
|---|---|---|---|---|
| suitability for extrusion: | | | | |
| Formulation A | acceptable | n.t. | n.t. | n.t. |
| Formulation B | no good | n.t. | n.t. | n.t. |

| run no. | 5 | 6 | 7 | 8 |
|---|---|---|---|---|
| duration of run, minutes | 8 | 8 | 5 | 17 |
| classifier wheel type | long cage | long cage | long cage | long cage |
| classifier wheel speed, rpm | 3000 | 2000 | 2000 | 3800 |
| feed pre-ground? | no | no | yes | yes |
| feed rate, kg/h | 259 | 451 | 554 | 152 |
| unacceptable build-up? | yes | yes | yes | yes |
| product characterization: | | | | |
| particle size[2], µm | 12.1 | 18.3 | 16.8 | 10.5 |
| specific surface area, cm$^2$/g | 1.28 | 1.01 | 1.10 | 1.38 |
| suitability for extrusion: | | | | |
| Formulation A | borderline | n.t. | borderline | borderline |
| Formulation B | no good | n.t. | no good | no good |

[1]in this run the air classifier motor burned out and the test was aborted
[2]Coulter Significant build-up occurred in all runs. Only one run generated powder that was suitable for downstream formulation by extrusion, and then for Formulation A but not for Formulation B. Average particle size achieved in runs 5 and 8 was less than 15 µm, yet suitability for extrusion was found to be only borderline for Formulation A and unacceptable for Formulation B. The Powderizer™ air classifying mill was judged from these tests to be an unsatisfactory apparatus for the size reduction step of the present process.

C. Pulvocron™ PC-20 air classifying mill

The Pulvocron™ PC-20 of Strong-Scott is described as an "air-swept hammer mill". It differs from other air classifying mills tested in being arranged with a horizontal axis of rotation, as well as utilizing a different design of rotor, or beater plate, and classifier wheel. The classifier wheel is independently driven. The ratio of air flow volume to weight of solid feed is high; furthermore the air flow is very turbulent and it is probable that size reduction by particle-particle collision occurs to a significant extent as well as by direct impact of particles on the beater plate. For present purposes, therefore, the Pulvocron™ can be considered an apparatus producing a turbulent high-velocity gas stream wherein particle-particle attrition occurs.

The Commander™ Model 2400 of Jacobson is a swing hammer mill which was used for pre-grinding flakes of drum dried ammonium glyphosate prior to milling in the Pulvocron™ air classifying mill.

In a series of twelve runs of the Pulvocron™, a number of parameters were varied including beater plate rotation speed (5340–6970 rpm), classifier wheel rotation speed (2000–5500 rpm), air flow (26.2–29.4 m³/minute) and feed rate (235–874 kg/h). In some runs the drum dried ammonium glyphosate was fed directly in the form of flakes and in some runs pre-ground ammonium glyphosate was used as the feed. Data are presented in the tables below (n.t.=not tested).

| run no. | 1 | 2 | 3 | 4 |
|---|---|---|---|---|
| duration of run, minutes | | 4 | 3 | 3 |
| beater plate speed, rpm | 7000 | 5340 | 6115 | 6115 |
| classifier wheel speed, rpm | 5000 | 2000 | 2000 | 3500 |
| air flow, m³/minute | 26.2 | 28.4 | 27.8 | 27.8 |
| feed pre-ground? | no | no | no | no |
| feed rate, kg/h | 235 | 757 | 874 | 611 |
| unacceptable build-up? | yes[1] | no | no | no |
| product characterization: | | | | |
| particle size[2], µm | n.t. | 15.6 | 13.5 | 11.2 |
| specific surface area, cm$^2$/g | n.t. | 1.47 | 1.17 | 1.34 |
| suitability for extrusion: | | | | |
| Formulation A | n.t. | acceptable | borderline | n.t. |
| Formulation B | n.t. | acceptable | no good | acceptable |

| run no. | 5 | 6 | 7 | 8 |
|---|---|---|---|---|
| duration of run, minutes | | | 25 | 22 |
| beater plate speed, rpm | 6915 | 6100 | 5300 | 5300 |
| classifier wheel speed, rpm | 4000 | 3500 | 2000 | 2000 |
| air flow, m³/minute | 29.4 | 28.1 | 28.5 | 28.2 |
| feed pre-ground? | yes | yes | yes | no |
| feed rate, kg/h | | 247 | 272 | 263 |
| unacceptable build-up? | yes[1] | yes | no | no |
| product characterization: | | | | |
| particle size[2], µm | n.t. | 7.9 | 8.4 | 8.2 |
| specific surface area, cm$^2$/g | n.t. | 2.10 | 2.31 | 1.85 |
| suitability for extrusion: | | | | |
| Formulation A | n.t. | acceptable | acceptable | acceptable |
| Formulation B | n.t. | borderline | no good | no good |

| run no. | 9 | 10 | 11 | 12 |
|---|---|---|---|---|
| duration of run, minutes | 18 | 15 | 15 | 30 |
| beater plate speed, rpm | 5300 | 6100 | 5300 | 5300 |
| classifier wheel speed, rpm | 2066 | 4060 | 5400 | 5500 |
| air flow, m³/minute | 28.2 | 28.2 | 28.2 | 27.4 |
| feed pre-ground? | no | no | no | yes |
| feed rate, kg/h | 263 | 278 | 263 | 310 |
| unacceptable build-up? | no | no | no | no |
| product characterization: | | | | |
| particle size[2], µm | 8.8 | 9.5 | 8.7 | 9.1 |
| specific surface area, cm$^2$/g | 1.91 | 1.81 | 2.07 | 2.14 |
| suitability for extrusion: | | | | |
| Formulation A | acceptable | borderline | acceptable | borderline |
| Formulation B | no good | n.t. | no good | n.t. |

[1]product melted in mill
[2]Coulter

Operating conditions were established for the Pulvocron™ that would result in efficient production of ammonium glyphosate powder having average particle size less than 15 µm. However, in spite of the small particle size, the product was found not to be suitable for downstream extrusion processing to make Formulation B, although the product of most runs was acceptable for making Formulation A.

D. Schutz-O'Neill Model 22H air classifying mill

The Schutz-O'Neill air classifying mill is similar to the Pulvocron™ but can be fitted with several rows of beater plates. The classifier wheel is mounted on the same shaft as the beater plates. The classifier is adjusted by changing a ring plate on the classifier and and by adjusting the recycle valve opening.

In a series of seven runs, parameters varied included diameter of ring plate (3 cm or 10 cm), recycle valve opening (5 cm or 12 cm) and feed rate (312–2813 kg/h). The mill was operated at a constant speed of 4600 rpm. In most runs, the feed was pre-ground using a Commander™ hammer mill as described above for the Pulvocron™. Data are presented in the tables below (n.t.=not tested).

| run no. | 1 | 2 | 3 | 4 |
|---|---|---|---|---|
| duration of run, minutes | 3 | 3 | 3 | 13 |
| ring plate diameter, cm | 3 | 3 | 10 | 3 |
| recycle valve opening, cm | 5 | 5 | 12 | 5 |
| feed pre-ground? | yes | yes | yes | yes |
| feed rate, kg/h | 1134 | 2269 | 2813 | 625 |
| unacceptable build-up? | no | no | no | no |
| product characterization: | | | | |
| particle size[1], µm | n.t. | 16.2 | 18.7 | 13.6 |
| specific surface area, cm²/g | n.t. | 1.29 | 1.09 | 1.43 |
| suitability for extrusion: | | | | |
| Formulation A | n.t. | n.t. | acceptable | n.t. |
| Formulation B | n.t. | n.t. | no good | n.t. |

| run no. | 5 | 6 | 7 |
|---|---|---|---|
| duration of run, minutes | 12 | 13 | 11 |
| ring plate diameter, cm | 3 | 3 | 3 |
| recycle valve opening, cm | 12 | 5 | 12 |
| feed pre-ground? | yes | no | no |
| feed rate, kg/h | 619 | 312 | 317 |
| unacceptable build-up? | no | no | no |
| product characterization: | | | |
| particle size[1], µm | 12.9 | 11.6 | 11.3 |
| specific surface area, cm²/g | 1.47 | 1.55 | 1.60 |
| suitability for extrusion: | | | |
| Formulation A | borderline | n.t. | borderline |
| Formulation B | n.t. | n.t. | no good |

[1]Coulter

Operating conditions were established for the Schutz-O'Neill air classifying mill that would result in efficient production of ammonium glyphosate powder having average particle size less than 15 µm. However, the product was found not to be generally suitable for downstream extrusion processing to make Formulation A or Formulation B, although one run did give a product that was acceptable for making Formulation A.

E. Prema™ Model CLM35 air classifying mill

The Prema™ air classifying mill of Prater Industries has an independently driven air classifier. It has an internal sieve ring to provide additional classification. The rotor is designed to provide two stages of milling within the same unit. Fine material produced in the first stage is discharged from the mill without passing through the second stage.

In a series of fourteen runs, parameters varied included rotor speed (5560–6650 rpm), classifier speed (2000–4800 rpm), air flow (18.8–27.2 $m^3$/minute) and feed rate (51–173 kg/h). In some runs, the feed was pre-ground using a Commander™ hammer mill as described above for the Pulvocron™. Data are presented in the tables below (n.t.= not tested).

| run no. | 1 | 2 | 3 | 4 | 5 |
|---|---|---|---|---|---|
| duration of run, minutes | 12 | 47 | 3 | 6 | 4 |
| rotor speed, rpm | 6628 | 6628 | 6628 | 6628 | 6628 |
| classifier wheel speed, rpm | 4800 | 4800 | 4000 | 4000 | 4000 |
| air flow, $m^3$/minute | 19.3 | 19.1 | 18.8 | 25.7 | 26.6 |
| feed pre-ground? | no | no | no | no | no |
| feed rate, kg/h | 53 | 51 | 95 | 55 | 55 |
| unacceptable build-up? | no | yes | no | no | no |
| product characterization: | | | | | |
| particle size[1], μm | n.t. | 6.3 | 7.4 | 8.6 | 8.6 |
| specific surface area, $cm^2/g$ | n.t. | 2.70 | 2.29 | 2.00 | 2.08 |
| suitability for extrusion: | | | | | |
| Formulation A | n.t. | n.t. | n.t. | n.t. | n.t. |
| Formulation B | n.t. | n.t. | n.t. | n.t. | n.t. |

| run no. | 6 | 7 | 8 | 9 | 10 |
|---|---|---|---|---|---|
| duration of run, minutes | 17 | 7 | 18 | 16 | 24 |
| rotor speed, rpm | 6628 | 6628 | 6628 | 6628 | 6628 |
| classifier wheel speed, rpm | 4000 | 4000 | 3000 | 2000 | 3000 |
| air flow, $m^3$/minute | 26.6 | 23.6 | 26.8 | 26.9 | 26.9 |
| feed pre-ground? | no | no | no | no | yes |
| feed rate, kg/h | 55 | 92 | 173 | 166 | 115 |
| unacceptable build-up? | no | yes[2] | no | no | yes |
| product characterization: | | | | | |
| particle size[1], μm | 9.3 | 9.1 | 11.2 | 17.1 | 12.7 |
| specific surface area, $cm^2/g$ | 2.16 | 1.92 | 1.65 | 1.07 | 1.44 |
| suitability for extrusion: | | | | | |
| Formulation A | acceptable | n.t. | borderline | borderline | n.t. |
| Formulation B | no good | n.t. | n.t. | n.t. | n.t. |

| run no. | 11 | 12 | 13 | 14 |
|---|---|---|---|---|
| duration of run, minutes | 26 | 26 | 16 | 29 |
| rotor speed, rpm | 6628 | 5560 | 5560 | 5560 |
| classifier wheel speed, rpm | 3000 | 3000 | 4022 | 3017 |
| air flow, $m^3$/minute | 26.9 | 27.2 | 27.0 | 27.1 |
| feed pre-ground? | yes | yes | yes | no |
| feed rate, kg/h | 103 | 103 | 59 | 93 |
| unacceptable build-up? | no | yes | no[3] | yes |
| product characterization: | | | | |
| particle size[1], μm | 14.0 | 14.4 | 10.5 | 11.2 |
| specific surface area, $cm^2/g$ | 1.24 | 1.31 | 1.68 | 1.79 |
| suitability for extrusion: | | | | |
| Formulation A | borderline | n.t. | n.t. | acceptable |
| Formulation B | n.t. | n.t. | n.t. | no good |

[1]Coulter
[2]product melted in mill
[3]run aborted because of mechanical problem The Prema™ mill could be operated in such a way as to provide a powder without unacceptable build-up of material in the mill; however under these conditions the powder produced was not generally suitable for downstream processing by extrusion. The product of some runs was acceptable for making Formulation A but not Formulation B.

F. Rotormill™ Model 3000

The Rotormill™ of International Process Equipment Co. has a rotor comprising a vertical axis carrying several sets of vanes and/or turboblades that create pockets of air rotating at very high velocity. Particles entering these pockets undergo size reduction by collision primarily with each other. Model 3000 has four sets of vanes and one set of turboblades, and also a classifier wheel rotated on the same axis as the vanes and turboblades.

In a series of seven runs, parameters varied included turboblade removal and feed rate. Rotor and classifier speed was constant at 2150 rpm. In one run, the feed was pre-ground using a Commander™ hammer mill as described above for the Pulvocron™. Data are presented in the tables below (n.t.=not tested).

| run no. | 1 | 2 | 3 | 4 |
|---|---|---|---|---|
| duration of run, minutes | 4 | 18 | 2 | 18 |
| turboblades removed? | no | no | no | no |
| feed pre-ground? | no | no | no | no |
| feed rate, kg/h | 1000 | 830 | | 640 |
| unacceptable build-up? | no | yes | yes[1] | no |
| product characterization: | | | | |
| particle size[2], μm | 16.8 | 13.4 | n.t. | 17.0 |
| specific surface area, cm²/g | 1.79 | 1.90 | n.t. | 1.03 |
| suitability for extrusion: | | | | |
| Formulation A | n.t. | very good | n.t. | borderline |
| Formulation B | n.t. | no good | n.t. | no good |

| run no. | 5 | 6 | 7[3] |
|---|---|---|---|
| duration of run, minutes | 3 | 15 | 5 |
| turboblades removed? | no | yes | |
| feed pre-ground? | no | no | no |
| feed rate, kg/h | | 640 | 317 |
| unacceptable build-up? | yes[1] | no | no |
| product characterization: | | | |
| particle size[2], μm | n.t. | 26.6 | 27.5 |
| specific surface area, cm²/g | n.t. | 0.68 | 0.77 |
| suitability for extrusion: | | | |
| Formulation A | n.t. | no good | borderline |
| Formulation B | n.t. | n.t. | n.t. |

[1]product melted in mill
[2]Coulter
[3]in this run, material was fed through mill twice Only one run of the Rotormill™ resulted in an average particle size smaller than 15 μm. Material from this run appeared suitable for downstream processing by extrusion to make Formulation A but not Formulation B. Removal of the turboblades helped the equipment to operate with fewer problems, but resulted in a significantly larger average particle size and poor downstream processability.

G. Micronizer™ jet mill

The Sturtevant Micronizer™ jet mill tested initially was an 8 inch (20 cm) model. Pre-grinding was conducted using a Sturtevant Simpactor™ pin mill or a Jacobson Commander™ hammer mill. In some runs ammonium glyphosate flakes were fed to the jet mill without pre-grinding.

The jet mill was tested with a stainless steel or polytetrafluoroethylene (PTFE) lined injection port, and with an alumina or polyurethane (PU) liner in the milling chamber. Feed rate was varied from 11 to 86 kg/h. Air flow in all runs was 3.65 m³/minute, supplied at 690 kPa. Later, a pilot-scale, 15 inch (36 cm) Micronizer™ jet mill was tested at a feed rate of 95 kg/h. Data are presented in the tables below (n.t.=not tested).

| run no. | 1 | 2 | 3 | 4 | 5 |
|---|---|---|---|---|---|
| size of jet mill (cm) | 20 | 20 | 20 | 20 | 20 |
| injection port material | steel | steel | steel | PTFE | PTFE |
| liner material | alumina | alumina | alumina | alumina | alumina |
| pre-grinding mill | none | none | none | pin | pin |
| feed rate, kg/h | 41 | 86 | 23 | 23 | 41 |
| unacceptable build-up? | no | no | no | no | no |
| product characterization: | | | | | |
| particle size, μm | 14.5[1] | 30.2[1] | 7.6[1] | 6.1[1] | 9.2[1] |
| specific surface area, cm²/g | n.t. | n.t. | 1.30 | 1.62 | n.t. |
| suitability for extrusion: | | | | | |
| Formulation A | n.t. | n.t. | n.t. | n.t. | n.t. |
| Formulation B | excellent | borderline | excellent | excellent | n.t. |

| run no. | 6 | 7 | 8 | 9 | 10 |
|---|---|---|---|---|---|
| size of jet mill (cm) | 20 | 20 | 20 | 20 | 20 |
| injection port material | PTFE | PTFE | steel | steel | steel |
| liner material | PU | PU | alumina | alumina | alumina |
| pre-grinding mill | no | no | hammer | hammer | hammer |
| feed rate, kg/h | 11 | 41 | 31 | 38 | 49 |
| unacceptable build-up? | no | no | no | no | no |
| product characterization: | | | | | |
| particle size, μm | 6.6[1] | 15.8[1] | 5.3[2] | 6.1[2] | 6.9[2] |
| specific surface area, cm²/g | 1.62 | 0.97 | 2.65 | 2.42 | 2.24 |
| suitability for extrusion: | | | | | |
| Formulation A | n.t. | n.t. | excellent | acceptable | borderline |
| Formulation B | excellent | n.t. | acceptable | acceptable | borderline |

| run no. | 11 | 12 | 13 | 14 | 15 |
|---|---|---|---|---|---|
| size of jet mill (cm) | 20 | 20 | 20 | 20 | 36 |
| injection port material | steel | steel | steel | steel | steel |
| liner material | alumina | alumina | alumina | alumina | alumina |
| pre-grinding mill | pin | pin | pin | none | hammer |
| feed rate, kg/h | 26 | 35 | 49 | 34 | 95 |
| unacceptable build-up? | no | no | no | no | no |

-continued

| run no. | 11 | 12 | 13 | 14 | 15 |
|---|---|---|---|---|---|
| product characterization: | | | | | |
| particle size, μm | 4.9[2] | 5.7[2] | 7.2[2] | 8.4[2] | 5.4[2] |
| specific surface area, cm$^2$/g | 2.70 | 2.51 | 2.13 | 2.14 | 2.31 |
| suitability for extrusion: | | | | | |
| Formulation A | acceptable | acceptable | borderline | borderline | very good |
| Formulation B | acceptable | n.t. | n.t. | borderline | very good |

[1]Brinkman
[2]Coulter

From these tests it was concluded that the Micronizer™ jet mill was a suitable apparatus for size reduction of ammonium glyphosate. The process ran with few problems and, if feed rate was not excessive, generated a product that was generally suitable for downstream processing by extrusion to make either Formulation A or Formulation B. In particular, the scale-up run (run no. 15) using a larger unit was very successful. The hammer mill was preferred over the pin mill for pre-grinding.

The preceding description of specific embodiments of the present invention is not intended to be a complete list of every possible embodiment of the invention. Persons skilled in this field will recognize that modifications can be made to the specific embodiments described here that remain within the scope of the present invention.

What is claimed is:

1. A process for preparing ammonium glyphosate powder, comprising the steps of
    (a) mixing (i) solid particulate glyphosate acid, (ii) water in an amount of about 0.5 to about 3 parts by weight per part by weight of glyphosate acid, and (iii) a base that supplies ammonium cations, in an amount of about 0.8 to about 1.25 mole equivalents of ammonia per mole of glyphosate acid, to form an aqueous reaction medium;
    (b) allowing the base to react with the glyphosate acid in the aqueous reaction medium to form a reaction product comprising a concentrated aqueous solution of ammonium glyphosate;
    (c) drying the reaction product to recover a particulate solid; and
    (d) accelerating the particulate solid in a turbulent high-velocity gas stream, to form by particle-particle attrition an ammonium glyphosate powder having a mean particle size of about 5 to about 20 μm.

2. The process of claim 1 wherein the order of mixing in step (a) is to mix the glyphosate acid and the water with agitation to form a slurry and thereafter to add to the slurry, with continued agitation, the base that supplies ammonium cations.

3. The process of claim 1 wherein the drying step comprises drying the reaction product by contact thereof with a heated surface to form a solid deposit on the heated surface and thereafter recovering the solid deposit in a particulate solid form.

4. The process of claim 3 wherein the drying step is performed with an apparatus of the drum dryer type.

5. The process of claim 1 wherein the step of accelerating the particulate solid in a turbulent high-velocity gas stream is performed using an apparatus of the fluid energy mill or jet mill type, and the gas stream is an air stream.

6. The process of claim 5 wherein the particulate solid recovered in the drying step is pre-ground by mechanical milling prior to fluid energy or jet milling.

7. A process for preparing a dry granular formulation comprising ammonium glyphosate and one or more surfactants, said process comprising the steps of
    (a) mixing (i) solid particulate glyphosate acid, (ii) water in an amount of about 0.5 to about 3 parts by weight per part by weight of glyphosate acid, and (iii) a base that supplies ammonium cations, in an amount of about 0.8 to about 1.25 mole equivalents of ammonia per mole of glyphosate acid, to form an aqueous reaction medium;
    (b) allowing the base to react with the glyphosate acid in the aqueous reaction medium to form a reaction product comprising a concentrated aqueous solution of ammonium glyphosate;
    (c) drying the reaction product to recover a particulate solid;
    (d) accelerating the particulate solid in a turbulent high-velocity gas stream, to form by particle-particle attrition an ammonium glyphosate powder having a mean particle size of about 5 to about 20 μm;
    (e) mixing about 75 to about 90 parts by weight of the ammonium glyphosate powder with about 10 to about 25 parts by weight of one or more surfactants, and with about 3 to about 10 parts by weight of water per 100 parts by weight of ingredients other than water, to form an extrudable wet mix;
    (f) extruding the wet mix to form extrudate strands that break to form moist coherent granules; and
    (g) drying the granules to produce the dry granular formulation.

8. The process of claim 7 wherein the order of mixing in step (a) is to mix the glyphosate acid and the water with agitation to form a slurry and thereafter to add to the slurry, with continued agitation, the base that supplies ammonium cations.

9. The process of claim 7 wherein the drying step comprises drying the reaction product by contact thereof with a heated surface to form a solid deposit on the heated surface and thereafter recovering the solid deposit in a particulate solid form.

10. The process of claim 9 wherein the drying step is performed with an apparatus of the drum dryer type.

11. The process of claim 7 wherein the step of accelerating the particulate solid in a turbulent high-velocity gas stream is performed using an apparatus of the fluid energy mill or jet mill type, and the gas stream is an air stream.

12. The process of claim 11 wherein the particulate solid recovered in the drying step is pre-ground by mechanical milling prior to fluid energy or jet milling.

13. The process of claim 7, further comprising a step (h) of classifying the dried granules to remove or recycle granules, fragments of granules and aggregates of granules that are outside a desired size range.

14. The process of claim 7, wherein the surfactant or surfactants are individually selected from those that are liquid or in a flowable state, in the absence of water or other solvent, at 25° C.

15. The process of claim 1, wherein the base that supplies the ammonium cations is selected from a group consisting of ammonium carbonate, ammonium bicarbonate, aqueous ammonia and anhydrous ammonia.

16. The process of claim 15, wherein the base that supplies the ammonium cations is aqueous ammonia or anhydrous ammonia.

17. The process of claim 1, wherein the amount of base added in step (a) is from about 0.95 to about 1.05 mole equivalents of ammonia per mole of glyphosate acid.

18. The process of claim 1, further comprising adding sodium sulfite to the reaction medium to inhibit nitrosamine formation.

19. The process of claim 1, wherein the concentration of ammonium glyphosate in the concentrated aqueous solution is from at least about 20% by weight to a concentration less than the solubility limit of ammonium glyphosate in the reaction medium.

20. The process of claim 1, wherein the concentration of ammonium glyphosate in the concentrated aqueous solution is from at least about 40% by weight to a concentration less than the solubility limit of ammonium glyphosate in the reaction medium.

21. The process of claim 1, wherein the concentration of ammonium glyphosate in the concentrated aqueous solution is from about 40% to about 60% by weight.

22. The process of claim 1, wherein the reaction product is maintained at a temperature of from about 65° C. to about 85° C.

23. The process of claim 1, wherein the mean particle size of the ammonium glyphosate powder is from about 5 $\mu$m to about 15 $\mu$m.

24. The process of claim 1, wherein the mean particle size of the ammonium glyphosate powder is from about 5 $\mu$m to about 10 $\mu$m.

25. The process of claim 1, wherein the mean particle size of the ammonium glyphosate powder is from about 7 $\mu$m to about 10 $\mu$m.

26. The process of claim 1, wherein the ammonium glyphosate powder has a specific surface area of from about 1.25 $m^2/g$ to about 3 $m^2/g$.

27. The process of claim 1, wherein the ammonium glyphosate powder has a specific surface area of from about 1.5 $m^2/g$ to about 3 $m^2/g$.

28. The process of claim 1, wherein the ammonium glyphosate powder has a specific surface area of from about 2.25 $m^2/g$ to about 3 $m^2/g$.

29. The process of claim 7, further comprising the step of admixing with said one or more surfactants a material selected from the group consisting of water, glycols, and mixtures thereof before adding said one or more surfactants to the paste.

30. The process of claim 7, wherein said one or more surfactants comprises at least one cationic surfactant or at least one amphoteric surfactant.

31. The process of claim 30, wherein said cationic surfactant or amphoteric surfactant is selected from the group consisting of alkylamines, alkylammonium salts, alkylamine oxides, alkylbetaines, alkyletheramines, alkyletherammonium salts, alkyletheramine oxides; and polyoxypropylene derivatives thereof; and mixtures thereof.

32. The process of claim 7, wherein said one or more surfactants comprises at least one alkyl polyglycoside surfactant.

33. The process of claim 7, wherein said one or more surfactants comprises at least one polyoxyethylene $C_{16-22}$ alkylether surfactant.

34. A process according to claim 7, wherein the extrudable wet mix formed in step (e) has a weight ratio of total surfactant to ammonium glyphosate of from about 1:9 to about 1:3.

* * * * *